United States Patent
Semturs et al.

(10) Patent No.: US 11,361,435 B2
(45) Date of Patent: Jun. 14, 2022

(54) PROCESSING FUNDUS IMAGES USING MACHINE LEARNING MODELS TO GENERATE BLOOD-RELATED PREDICTIONS

(71) Applicant: Google LLC, Mountain View, CA (US)

(72) Inventors: Christopher Semturs, Ottenbach (CH); Dale R. Webster, San Mateo, CA (US); Avinash Vaidyanathan Varadarajan, Los Altos, CA (US); Akinori Mitani, Menlo Park, CA (US); Lily Hao Yi Peng, Mountain View, CA (US)

(73) Assignee: Google LLC, Mountain View, CA (US)

(*) Notice: Subject to any disclaimer, the term of this patent is extended or adjusted under 35 U.S.C. 154(b) by 71 days.

(21) Appl. No.: 16/835,152

(22) Filed: Mar. 30, 2020

(65) Prior Publication Data

US 2020/0311933 A1  Oct. 1, 2020

Related U.S. Application Data

(60) Provisional application No. 62/826,832, filed on Mar. 29, 2019.

(51) Int. Cl.
*G06K 9/00* (2022.01)
*G06T 7/00* (2017.01)
(Continued)

(52) U.S. Cl.
CPC ............ *G06T 7/0012* (2013.01); *G06N 3/04* (2013.01); *G16H 10/60* (2018.01);
(Continued)

(58) Field of Classification Search
CPC .. H04B 17/309; H04B 7/0617; H04B 7/0626; H04B 7/0695; H04B 7/088; H04L 5/0023; H04L 5/0048; H04W 16/28; H04W 24/00; H04W 72/042; H04W 72/046; H04W 76/27; H04W 88/08; G06N 3/04; G06T 2207/20081; G06T 2207/20084; G06T 2207/30041; G06T 2207/30101; G06T 7/0012; G16H 10/60
See application file for complete search history.

(56) References Cited

U.S. PATENT DOCUMENTS 6,006,119 A    12/1999  Soller et al.
2013/0301901 A1*  11/2013  Satish .................... G01N 21/84
                                                    382/134
(Continued)

FOREIGN PATENT DOCUMENTS

WO   WO 2018/035473   2/2018
WO   WO 2018/201632   11/2018

OTHER PUBLICATIONS

Aisen et al, "Retinal Abnormalities Associated With Anemia" Archives of Ophthalmology, Mar. 1984, 102(3):358.
(Continued)

*Primary Examiner* — Xin Jia
(74) *Attorney, Agent, or Firm* — Fish & Richardson P.C.

(57) ABSTRACT

Methods, systems, and apparatus, including computer programs encoded on computer storage media, for processing fundus images using fundus image processing machine learning models.

21 Claims, 5 Drawing Sheets

(51) Int. Cl.
  *G16H 10/60* (2018.01)
  *G06N 3/04* (2006.01)
(52) U.S. Cl.
  CPC .............. *G06T 2207/20081* (2013.01); *G06T 2207/20084* (2013.01); *G06T 2207/30101* (2013.01)

(56) References Cited

U.S. PATENT DOCUMENTS

| | | | |
|---|---|---|---|
| 2019/0216333 A1* | 7/2019 | Lai | G06F 16/55 |
| 2019/0221313 A1* | 7/2019 | Rim | G06T 7/00 |
| 2020/0085290 A1 | 3/2020 | Wang et al. | |

OTHER PUBLICATIONS

Barker et al, "The measurement of dyshemoglobins and total hemoglobin by pulse oximetry" Current Opinion in Anaesthesiology, 21(6):805-810, 2008.
Barker et al., "Continuous Noninvasive Hemoglobin Monitoring: A Measured Response to a Critical Review", Anesth Analg., Feb. 2016, 122(2):565-572.
Bland et al., "Measuring agreement in method comparison studies", Statistical Methods in Medical Research, Jun. 1999, 8(2):135-160.
Bosman et al, "Anemia with erythropoietin deficiency occurs early in diabetic nephropathy" Diabeters Care, Mar. 2001, 24(3):495-499.
Caruana et al, "Overfitting in Neural Nets Backpropagation, Conjugate Gradient, and Early Stopping" Advances in Neural Information Processing Systems, 2001, 7 pages.
Christopher et al., "Performance of Deep Learning Architectures and Transfer Learning for Detecting Glaucomatous Optic Neuropathy in Fundus Photographs", Scientific Reports, Nov. 2018, 8(16685):1-13.
Conlin et al., "Nonmydriatic teleretinal imaging improves adherence to annual eye examinations in patients with diabeters", J Rehabil Res Dev., Oct. 2006, 43(6):733-740.
Craig et al, "Anemia and Diabetes in Absence of Nephropathy" Diabetes Care, May 2005, 28(5):1118-1123.
Davis et al, "Risk factors for high-risk proliferative diabetic retinopathy and severe visual loss: Early Treatment Diabetic Retinopathy Study Report #18" Invest Ophthalmol Vis Sci., Feb. 1998, 39(2):233-252.
Garg et al, "Telemedicine and retinal imaging for improving diabetic retinopathy evaluation" Arch Intern Med., Nov. 2012, 172(21):1677-1680.
Gehring et al., "Accuracy of point-of-care-testing (POCT) for determining hemoglobin concentrations", Acta Anesthesia Scand, Sep. 2002, 46(8):980-986.
Gulshan et al., "Development and Validation of a Deep Learning Algorithm for Detection of Diabetic Retinopathy in Retinal Fundus Photographs", JAMA, Dec. 2016, 316(22):2402-2410.
Hiscock et al, "Systematic review and meta-analysis of method comparison studies of Masimo pulse co-oximeters (Radical-7TM or Pronto-7TM) and HemoCue absorption spectrometers (B-Hemoglobin or 201+) with laboratory hemoglobin estimation" Anaesth Intensive Care, May 2015, 43(3):341-350.
Holland et al, "Predictors of hospitalization and death among pre-dialysis patients a retrospective cohort study" Nephrol Dial Transplant, May 2000, 15(5):650-658.
Horwich et al, "Anemia is associated with worse symptoms, greater impairment in functional capacity and a significant increase in mortality in patients with advanced heart failure" J Am Coll Cardiol, Jun. 2002, 39(11):1780-1786.
Kalantri et al. "Accuracy and reliability of pallor for detecting anaemia: a hospital-based diagnostic accuracy study" PLoS One, 5(1):e8545, Jan. 2010, 6 pages.
Kasper et al," Harrison's Principles of Internal Medicine" McGraw Hill Professional, 2018, 864 pages.
Kim et al, "Accuracy of continuous noninvasive hemoglobin monitoring: a systematic review and meta-analysis" Anesth Analg., Aug. 2014, 119(2):332-346.
Krause et al., "Grader Variability and the Importance of Reference Standards for Evaluating Machine Learning Models for Diabetic Retinopathy", Ophthalmology, Aug. 2018, 125(8):1264-1272.
Krizhevsky et al, "Imagenet classification with deep convolutional neural networks Advances in Neural Information Processing Systems" 2012, 9 pages.
LeCun et al. "Deep learning" Nature, May 2015, 521:436-444.
Li et al., "Efficacy of a Deep Learning System for Detecting Glaucomatous Optic Neuropathy Based on Color Fundus Photographs", Ophthalmology, Aug. 2018, 125(8):1199-1206.
Liu et al., "A Deep Learning-Based Algorithm Identifies Glaucomatous Discs Using Monoscopic Fundus Photographs", Ophthalmology Glaucoma, Jul. 2018, 1(1):15-22.
Mannino et al, "Smartphone app for non-invasive detection of anemia using only patient-sourced photos" Nature Communications, 9(4924), Dec. 2018, 10 pages.
Mehdi et al, "Anemia, Diabetes, and Chronic Kidney Disease" Diabetes Care, Jul. 2009, 32(7):1320-1326.
Milman, "Anemia-still a major health problem in many parts of the world!" Annals of Hematology, Jul. 2011, 90(4):369-377.
Opitz et al, "Popular Ensemble Methods: An Empirical Study" J Artif Intell Res, Dec. 1999.
PCT International Search Report and Written Opinion in International Application No. PCT/US2020/025819, dated Jul. 10, 2020, 15 pages.
Pinto et al, "The new noninvasive occlusion spectroscopy hemoglobin measurement method: a reliable and easy anemia screening test for blood donors", Blood Transfusion, Oct. 2014, 12(4):458-463.
Poplin et al., "Prediction of cardiovascular risk factors from retinal fundus photographs via deep learning", Ature Biomedical Engineering, Feb. 2018, 2(3):158-164.
Posey, The Ocular Manifestations of Anemia, JAMA, July 1897, 29(4):169-171.
Priya et al, "Large Minibatch SGD: Training ImageNet in 1 Hour" arXiv, Apr. 2018, 12 pages.
Shah et al "Accuracy of noninvasive hemoglobin and invasive point-of-care hemoglobin testing compared with a laboratory analyzer" Intentional Journal of Laboratory Hematology, Feb. 2014, 36(1):56-61.
Sheard et al., "UK Biobank Haematology Data Companion Document", Biobank, Oct. 2017, 15 pages.
Singh et al, "Erythropoietic stress and anemia in diabetes mellitus" Nat Rev Endocrinol, Apr. 2009, 5(4):204-210.
Smith Jr. "The Clinical and Economic Burden of Anemia", The American Journal of Managed Care, Mar. 2010, 16(3):S59-S66.
Stevens et al. "Global, regional, and national trends in hemoglobin concentration and prevalence of total and severe anaemia in children and pregnant and non-pregnant women for 1995-2011: a systematic analysis of population-representative data" Lancet Glob Health, Jul. 2013, 1(1):E16-E25.
Stoltzfus, "Summary: Implications for Research and Programs" American Society for Nutritional Sciences, Feb. 2001, 131(2):697S-701S.
Sutskever et al, "On the importance of initialization and momentum in deep learning" International Conference on Machine Learning, 2013, 28:1-14.
Szegedy et al, "Inception-v4, Inception-ResNet and the Impact of Residual Connections on Learning" arVix, Aug. 2016, 12 pages.
Szegedy et al, "Rethinking the Inception Architecture for Computer Vision" arXiv, 2015, 10 pages.
TensorFlow [online], "BibTex Citation" retrieved on Jul. 31, 2020 retrieved from URL <https://chromium.googlesource.com/external/github.com/tensorflow/tensorflow/+/refs/heads/0.6.0/tensorflow/g3doc/resources/bib.md>, 2 pages.
Thomas et al, "Unrecognized anemia in patients with diabetes: a cross-sectional survey" Diabetes Care, Apr. 2003, 26(4):1164-1169.
Thomas, "Anemia in diabetes: marker or mediator of microvascular disease?" Nature Clinical Practice Nephrology, Jan. 2007, 3(1):20-30.

(56) References Cited

OTHER PUBLICATIONS

Ting et al., "Development and Validation of a Deep Learning System for Diabetic Retinopathy and Related Eye Diseases Using Retinal Images From Multiethnic Populations With Diabetes", JAMA, Dec. 2017, 318(22):2211-2223.

Tsan et al, "Assessment of diabetic teleretinal imaging program at the Portland Department of Veterans Affairs Medical Center" J Rehabil Res Dev, Feb. 2015, 52(2):193-200.

UKBioBank.ac.uk [online], "About UK Biobank" Jun. 17, 2020, retrieved on Jul. 31, 2020, retrieved from URL <https:1/www.ukbiobank.ac.uk/about-biobank-uk/>, 6 pages.

UKBioBank.ac.uk [online], "Category 100081", retrieved on Jul. 31, 2020, retrieved from URL <https://biobank.ctsu.ox.ac.uk/crystal/label.cgi?id= 100081>, 2 pages.

Varadarajan et al., "Deep Learning for Predicting Refractive Error From Retinal Fundus Images", Invest Ophthalmol Vis Sci., Jun. 2018, 59(7):2861-2868.

WHO, "Haemoglobin concentrations for the diagnosis of anaemia and assessment of severity" VMNIS, 2011, 6 pages.

WHO, "Worldwide prevalence of anaemia 1993-2005", WHO Global Database on Anaemia, Jul. 2018, 51 pages.

Wittenmeier et al. "Comparison of the gold standard of hemoglobin measurement with the clinical standard (BGA) and noninvasive hemoglobin measurement (SpHb) in small children: a prospective diagnostic observational study" Pediatric Anesthesia, Oct. 2015, 25(10):1046-1053.

PCT International Preliminary Report of Patentability in International Application No. PCT/2020/025819, dated Oct. 14, 2021, 8 pages.

\* cited by examiner

| Technique | (Estimated) MAE |
|---|---|
| Hematology analyzer | .14 g/dL |
| Invasive point-of-care devices | .51 g/dL |
| Non-invasive point-of-care devices | 1.1 g/dL |
| Smartphone-based method | .96 g/dL |
| Our method (combined model) | .63 (.62 to .64) g/dL |

PROCESSING FUNDUS IMAGES USING MACHINE LEARNING MODELS TO GENERATE BLOOD-RELATED PREDICTIONS

CROSS-REFERENCE TO RELATED APPLICATION

This application claims priority to U.S. Provisional Application No. 62/826,832, filed on Mar. 29, 2019. The disclosure of the prior application is considered part of and is incorporated by reference in the disclosure of this application.

BACKGROUND

This specification relates to processing images using a machine learning model.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification generally describes a system that generates health analysis data for a patient by processing data that includes one or more fundus images of the patient using a fundus image processing machine learning model to generate a prediction that relates to the blood of the patient, e.g., to predict a property of the blood of the patient or to directly predict the current condition of the patient with respect to anemia.

Particular embodiments of the subject matter described in this specification can be implemented so as to realize one or more of the following advantages. Accurately measuring the properties of a patient's blood is important for effective patient treatment, e.g., for accurately assessing a patient's current condition or making accurate diagnoses for various diseases. For example, the current level of hemoglobin in a patient's blood is a reliable indicator of anemia. However, conventional techniques for measuring these properties, e.g., collecting venous or capillary blood samples, are invasive and painful, can cause infection of patients and healthcare workers, and generate biohazardous waste. The described systems, on the other hand, accurately predict certain properties of blood in a non-invasive manner, i.e., using only a fundus image of the fundus of the patient's eye (or two fundus images, one of each of the patient's eyes). In particular, as shown in the experimental results outlined in FIG. 3A below, the described systems achieve results in measuring various properties of a patient's blood that are comparable to conventional invasive techniques that require a blood sample and significantly better than other existing non-invasive techniques. Moreover, as shown in FIG. 3B below, the described techniques can be used to accurately predict the patient's current condition with respect to anemia from only one or more fundus images of the eye of the patient (and, optionally, other patient data).

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification generally describes a system that can generate health analysis data for a patient from an input that includes one or more fundus images of the patient and, optionally, other patient data. A fundus image is a photograph of the fundus of one of the eyes of the patient. The fundus of an eye is the interior surface of the eye opposite the lens and includes, among other things, the retina and the optic disc.

Generally, to generate the health analysis data for a given patient, the system processes the one or more fundus images and, optionally, the other patient data using a fundus image processing machine learning model to generate a model output for the patient and then generates the health analysis data from the model output. As will be described in more detail below, in some implementations the model output predicts the current condition of the patient with respect to anemia while in other implementations the model output is a predicted property of the blood of the patient.

Figure 1:
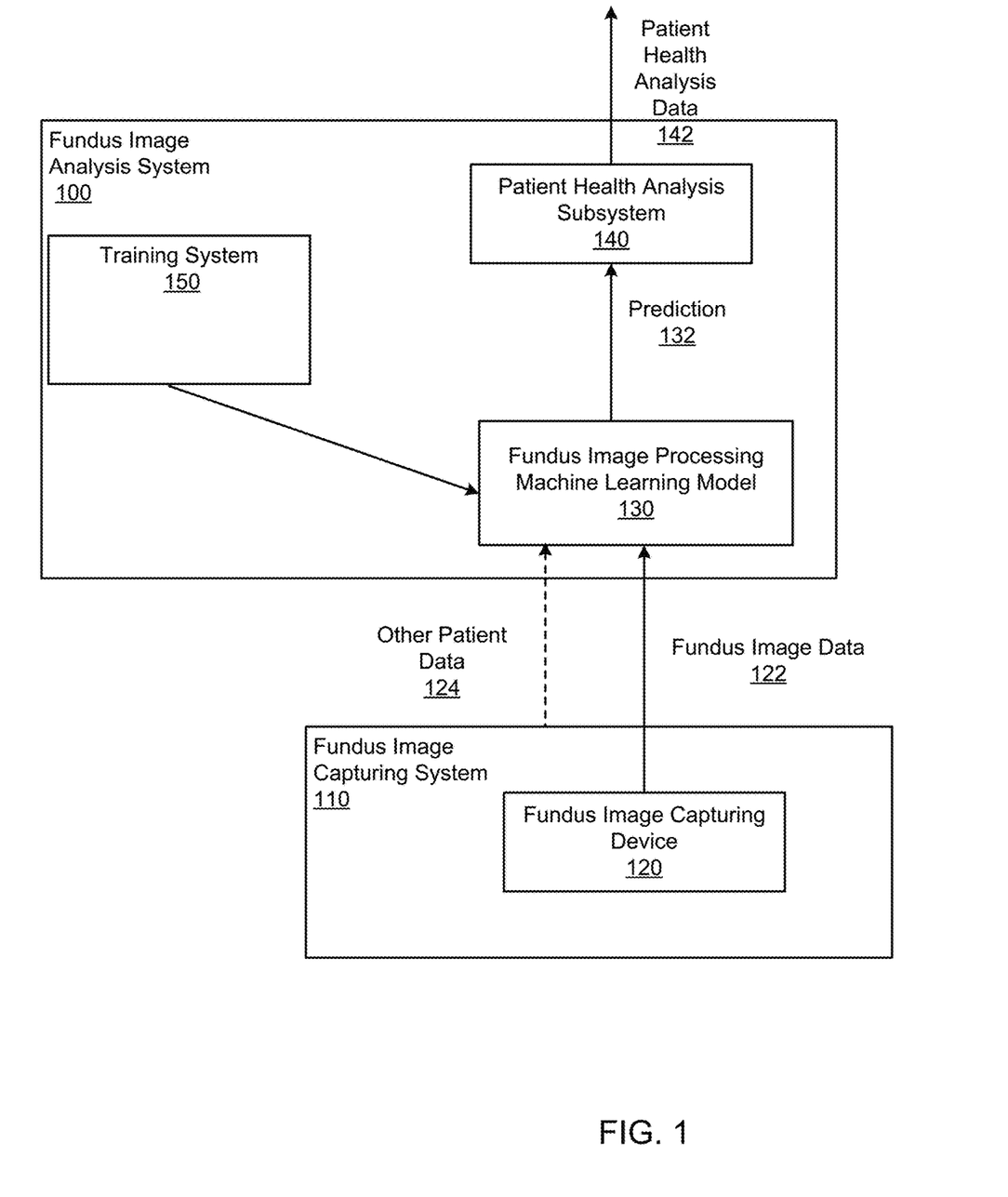
FIG. 1 shows an example fundus image analysis system.

FIG. 1 shows an example fundus image analysis system 100. The fundus image analysis system 100 is an example of a system implemented as computer programs on one or more computers in one or more locations, in which the systems, components, and techniques described below can be implemented.

For a given patient, the fundus image analysis system 100 receives fundus image data 122 that includes one or more fundus images of the patient's eye and generates health analysis data 142 that characterizes the health of the patient using the fundus image data 122.

In some implementations, the fundus image analysis system 100 includes or is in communication with a fundus image capturing system 110 that generates the fundus images and provides them as input fundus image data 122 to the fundus image analysis system. In particular, the fundus image capturing system 110 includes one or more image capturing devices, e.g., an image capturing device 120, that are configured to capture images of the fundus of a patient. Generally, the image capturing device 120 is a specialized fundus camera that is configured to capture an appropriate type of fundus image, e.g., using color fundus photography, stereoscopic photography, wide field or ultra wide field photography, or scanning laser ophthalmoscopy (SLO). In some cases, the image capturing system 110 includes multiple image capturing devices that capture different types of fundus images.

In other implementations, the fundus image analysis system 100 receives the input fundus image data 122 from an external system, e.g., over a data communication network.

The fundus image analysis system 100 processes a model input that includes the input fundus image data 122 and, optionally, the other data for the given patient using a fundus image processing machine learning model 130. The fundus image processing machine learning model 130 is a machine learning model that is configured to process the model input to generate a prediction 132 that relates to the blood of the patient.

In some implementations, the fundus image processing machine learning model 130 is a single neural network that generates a single model output. In some other implementations, the fundus image processing machine learning model 130 is an ensemble of neural networks that each generate a respective model output for a received input. When the system 100 employs an ensemble of neural networks, each neural network in the ensemble is configured to receive the same kind of input and generate the same kind of output as the other neural networks in the ensemble but has been trained on different training data from each other neural network in the ensemble.

The fundus image analysis system 100 also includes a patient health analysis subsystem 140 that receives the prediction 132 and generates the patient health analysis data 142. Generally, the patient health analysis subsystem 140 generates health analysis data that characterizes the model output in a way that can be presented to a user of the system. The patient health analysis subsystem 140 can then provide the health analysis data 142 for presentation to the user in a user interface, e.g., on a user computer of the patient or on a computer of a medical professional, store the health analysis data 142 for future use, or provide the health analysis data 142 for use for some other immediate purpose.

In some implementations, the fundus image analysis system 100 receives requests for patient health analysis data 142 from remote users of user computers over a data communication network. For example, a user computer, e.g., a computer on which the fundus image capturing system 110 is implemented, may be able to submit a request to the fundus image analysis system 100 over the data communication network by providing fundus image data as part of making an Application Programming Interface (API) call to the fundus image analysis system 100. In response to the API call, the fundus image analysis system 100 can generate the health analysis data 142 and transmit the health analysis data to the user computer over the data communication network.

Additionally, in some implementations, the machine learning model 130 is implemented by one or more computers that are remote from the fundus image analysis system 100. In these implementations, the fundus image analysis system 100 can access the machine learning model 130 by making an API call over a network that includes the input to the machine learning model 130 and can receive the model output 132 in response to the API call.

When included, the other patient data 124 for the patient may include demographic data for the patient. Examples of demographic data that could be received by the system include any one or more of ethnicity, age, sex, current smoking status, systolic and diastolic blood pressure, pulse rate, height, weight, and/or body mass index.

As described above, the system 100 processes the model input using one or more neural networks that each generate a model output for the input.

In some cases, the model output is a predicted property of the blood of the patient. In these cases, each neural network generates a regression output, i.e., directly predicts the value of the property. As a particular example, the property can be a level of hemoglobin in the blood of the patient. As another example, the property can be the hematocrit of the blood of the patient. As yet another example, the property can be the red blood cell count in the blood of the patient.

In some other cases, the model output predicts the current condition of the patient with respect to anemia. In these cases, each neural network generates a classification output, i.e., generates a probability for each of one or more classes. For example, the model can generate a probability for a single class, i.e., a probability of whether the patient has anemia. As another example, the model can generate a probability for multiple different anemia classes, each of which represents a different state of the disease. For example, the multiple different anemia classes can include one or more of: anemia, approximate anemia, or moderate anemia.

When the model input does not include any other patient data, for each neural network, the system 100 processes the fundus image through a convolutional neural network to generate a convolutional output, i.e., the output of the final convolutional layer in the convolutional neural network or a combination of the outputs of multiple convolutional layers in the network when the model includes one or more final skip connections or residual connections. An example of a deep convolutional neural network that can be trained to process a fundus image to generate the model outputs described in this specification is described in Szegedy, Christian et al. "Going deeper with convolutions." Proceedings of the IEEE Conference on Computer Vision and Pattern Recognition, 2015. Other examples of deep convolutional neural networks, including convolutional neural networks with residual connections, that can be trained to process a fundus image to generate the model outputs described in this specification are described in Szegedy, Christian, et al. "Inception-v4, Inception-ResNet and the Impact of Residual Connections on Learning," available at http://arxiv.org/abs/1602.07261.

The system 100 then processes the convolutional output through one or more fully-connected layers to generate the model output for the neural network. For example, when the model output is a regression output the output layer of the neural network can be a linear layer that directly generates the regressed value of the property of the blood. When the model output is a classification output, the output layer of the neural network can be a softmax layer that generates the probabilities for the one or more classes.

When the model input does include other patient data, for each neural network, the system 100 processes the fundus image through a convolutional neural network to generate a convolutional output, i.e., the output of the final convolutional layer in the convolutional neural network or a combination of the outputs of multiple convolutional layers in the network when the model includes a final skip connection or residual connection. The system 100 then processes the convolutional output and (i) the other patient data or (ii) data derived from the other patient data through one or more fully-connected layers to generate the model output for the neural network.

When data derived from the other patient data is the data that is being processed, the system 100 can generate the derived data by processing the other patient data through one or more neural network layers or by applying a learned weight matrix to the other patient data.

The system 100 then generates a final prediction 132 for the patient from at least the model output. For example, when there is a single neural network, the system 100 can generate a model output for a fundus image of the patient's other eye and then combine, e.g., average, the two model outputs to generate the final prediction 132.

As another example, when there is an ensemble of neural networks, the system 100 can process the model input (and, optionally, also the model input for the patient's other eye) using all of the neural networks in the ensemble and the combine, e.g., average or concatenate, all of the model outputs generated by all of the neural networks in the ensemble to generate the final prediction 132.

Optionally, prior to processing the fundus image data using the neural network, the system 100 can pre-process the fundus images, i.e., the fundus images in the model input are pre-processed fundus images generated from raw fundus images received by the system. For example, for a given image, the system 100 can apply any of a variety of conventional image processing techniques to the image to improve the quality of the output generated by the machine learning model. As an example, the system 100 may crop, scale, deskew or re-center the image. As another example, the system 100 can remove distortion from the image, e.g., to remove blurring or to re-focus the image, using conventional image processing techniques.

Figure 2A:
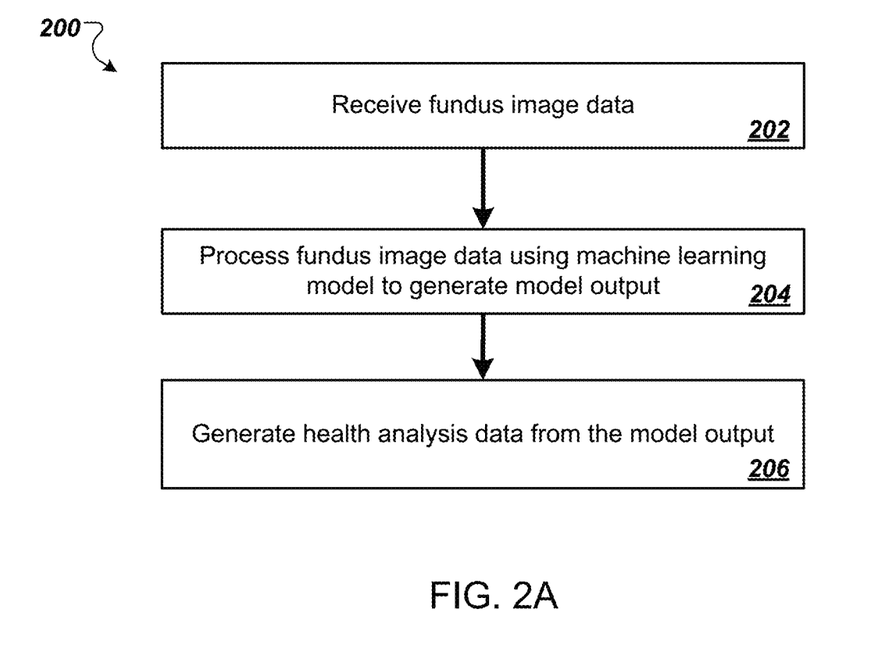
FIG. 2A is a flow diagram of an example process for generating health analysis data.

FIG. 2A is a flow diagram of an example process 200 for generating health analysis data. For convenience, the process 200 will be described as being performed by a system of one or more computers located in one or more locations. For example, a fundus image analysis system, e.g., the fundus image analysis system 100 of FIG. 1, appropriately programmed, can perform the process 200.

The system receives input fundus image data and, optionally, other patient data (step 202).

Generally, the fundus image data includes one or more fundus images of a patient's eye.

In some implementations, the fundus image data includes a single fundus image, e.g., an image that captures the current state of the patient's fundus.

The system processes a model input that includes the input fundus image data and, optionally, the other patient data using a fundus image processing machine learning model to generate a model output (step 204).

Optionally, prior to processing the fundus image data using the machine learning model, the system can pre-process the fundus images. For example, for a given image, the system can apply any of a variety of conventional image processing techniques to the image to improve the quality of the output generated by the machine learning model. As an example, the system may crop, scale, deskew or re-center the image. As another example, the system can remove distortion from the image, e.g., to remove blurring or to re-focus the image, using conventional image processing techniques.

In some implementations, the fundus image data includes multiple fundus images that capture the current state of the patient's fundus. For example, the fundus image data can include one or more images of the fundus in the patient's left eye and one or more images of the fundus in the patient's right eye. In these implementations, the system can process a respective model input for each of the fundus image to generate a respective model output for each of the neural networks in the ensemble.

The system generates health analysis data from the model output (step 206). That is, the system generates a prediction by combining the model outputs and then generates the health analysis data from the prediction. Generally, the health analysis data characterizes the model output in a way that can be presented to a user of the system. For example, the health analysis data can include a user interface presentation that presents the predicted measurement or the prediction with respect to anemia that is generated by the model.

In some implementations, the health analysis data also includes data derived from an intermediate output of the machine learning model that explains the portions of the fundus image or images that the machine learning model focused on when generating the model output. In particular, in some implementations, the machine learning model includes an attention mechanism that assigns respective attention weights to each of multiple regions of an input fundus image and then attends to features extracted from those regions in accordance with the attention weights. In these implementations, the system can generate data that identifies the attention weights and include the generated data as part of the health analysis data. For example, the generated data can be an attention map of the fundus image that reflects the attention weights assigned to the regions of the image. For example, the attention map can be overlaid over the fundus image to identify the areas of the patient's fundus that the machine learning model focused on when generating the model output.

The system can then provide the health analysis data for presentation to the user in a user interface, e.g., on a user computer of the patient or on a computer of a medical professional, or store the health analysis data for future use.

Figure 2B:
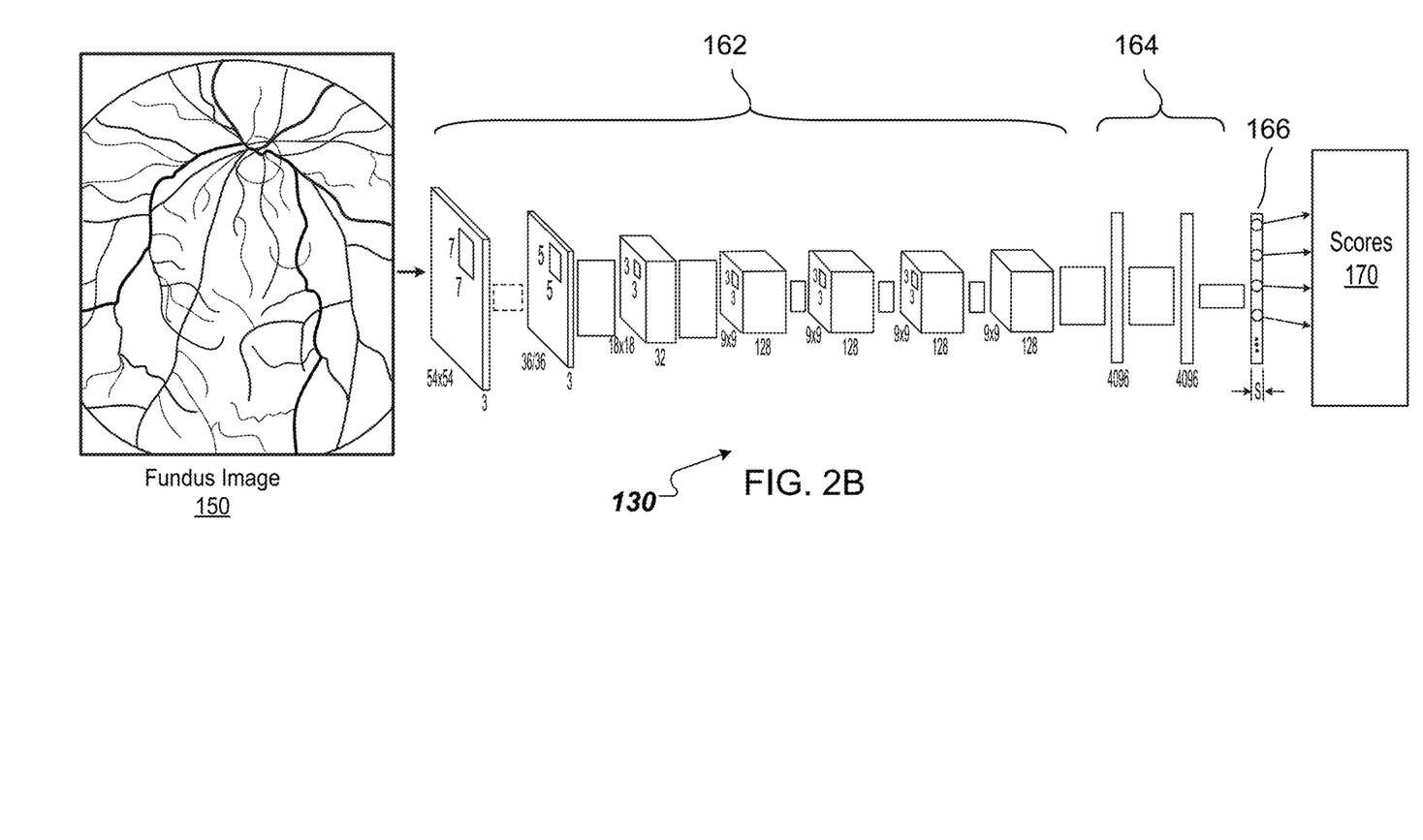
FIG. 2B shows the processing of an example fundus image by the fundus image processing machine learning model.

FIG. 2B shows the processing of an example fundus image 150 by the fundus image processing machine learning model 130. In particular, in the example of FIG. 2B, the fundus image processing machine learning model 130 is a deep convolutional neural network that is configured to receive the fundus image 150 and to process the fundus image 150 to generate a model output that characterizes a particular aspect of the patient's health.

The convolutional neural network illustrated in FIG. 2B is a simplified example of a deep convolutional neural network and includes a set of convolutional neural network layers 162, followed by a set of fully connected layers 164, and an output layer 166. It will be understood that, in practice, a deep convolutional neural network may include other types of neural network layers, e.g., pooling layers, normalization layers, and so on, and may be arranged in various configurations, e.g., as multiple modules, multiple subnetworks, and so on.

During the processing of the fundus image 150 by the convolutional neural network, the output layer 166 receives an output generated by the last fully connected layer in the set of fully connected layers 164 and generates the model output for the fundus image 150. In the example of FIG. 2B, the model output is a set of scores 170, with each score being generated by a corresponding node in the output layer 166. For example, the set of scores can include a set of scores for multiple anemia classifications, as described above.

Once the set of scores 170 have been generated, the fundus image analysis system generates patient health analysis data that characterizes an aspect of the patient's health from the scores 170 and provides the health analysis data for presentation to the user in a user interface, e.g., on a user computer of the patient or on a computer of a medical professional, stores the health analysis data for future use, or provides the health analysis data for use for some other immediate purpose.

In order to allow the model 130 to be used to effectively make predictions, the system trains the model 130 on training data that includes model inputs and ground truth model outputs for the model inputs, i.e., outputs that should be generated by the model 130 by processing the corresponding model inputs. In some implementations, the system or another system can first pre-train the convolutional neural network on a different, larger data set, e.g., an image classification data set such as ImageNet. When the model generates regression outputs, the system can train the model to minimize a regression loss function, such as mean squared error loss function, a mean absolute error loss function, a Huber Loss function or the like. When the model generates classification outputs, the system can train the model to minimize a classification loss function, such as a cross entropy loss function, a logistic loss, a mean squared error, a hinge loss or the like. Training the model to minimize a loss function may comprise iteratively applying an optimization procedure to the loss function to update parameters of the model (e.g., weights and/or biases of the model). The optimization procedure may be iterated until a threshold condition is satisfied, such as a threshold number of iterations, a threshold number of training epochs or a threshold accuracy on a test data set being reached. As a particular example, the system can train the model to minimize one of these loss functions using mini-batch stochastic gradient descent with momentum with linear warm up and with early stopping to prevent overfitting.

When the model includes an ensemble of neural networks, the system can train each neural network in the ensemble to minimize the same loss function but on different training data, i.e., different portions of a larger training set, on the same training set but with the model inputs sampled in different orders, or on overlapping portions of the larger training set.

Figure 3A:
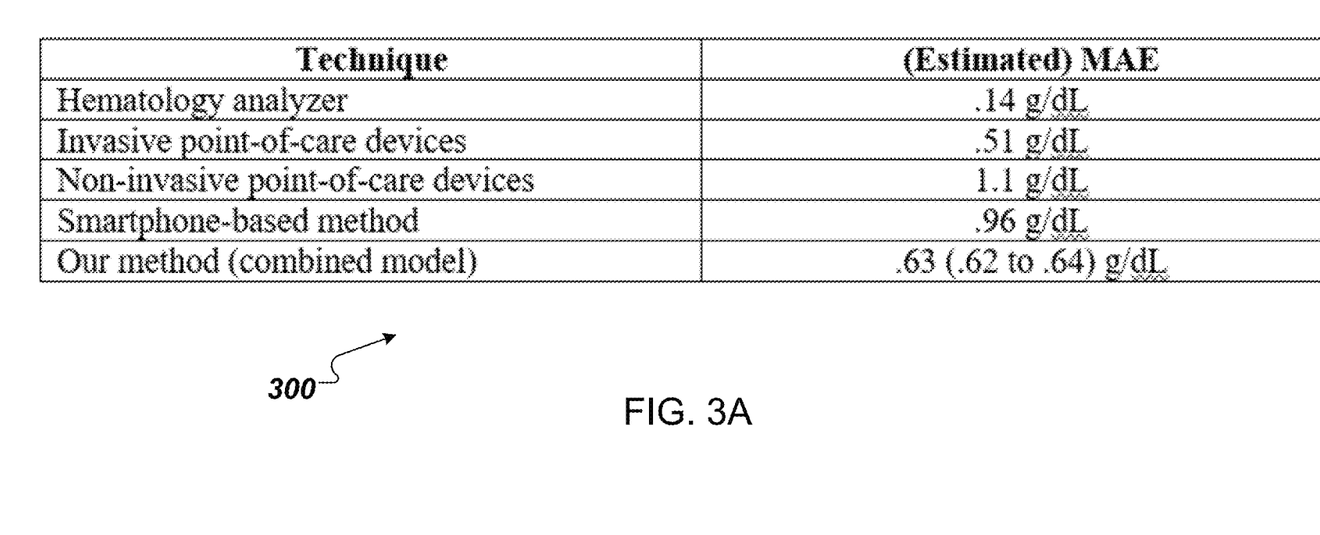
FIG. 3A is a chart that shows the accuracy of different methods to measure hemoglobin concentration.
Figure 3B:
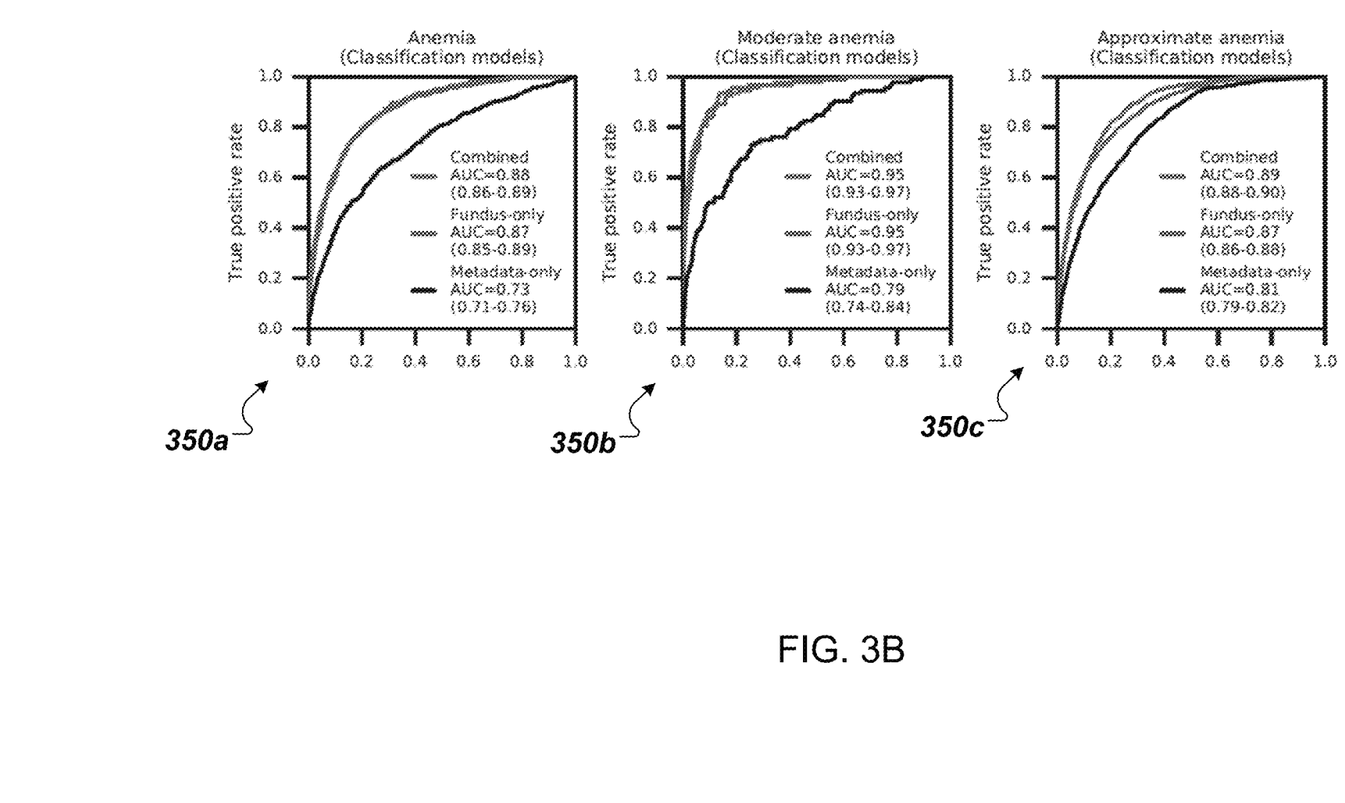
FIG. 3B shows the accuracy of the described systems in predicting patient anemia.

FIG. 3A is a chart 300 that shows the accuracy of different methods to measure hemoglobin concentration. In particular, FIG. 3A shows the estimated mean absolute error (MAE) (estimated assuming that the error has a Gaussian distribution) in measurements of hemoglobin concentration for five different methods: laboratory hematology analysis (the gold standard in hemoglobin concentration measurement), invasive point-of-care devices, non-invasive point-of-care devices, a smartphone-based method, and the described techniques (in particular a technique that processes two fundus images and other patient data, referred to as the "combined model"). From the MAEs for the various methods, it can be seen that the described techniques generate more accurate hemoglobin concentration measurements than either of the other two non-invasive methods (non-invasive point-of-care devices and smartphone-based methods) while having comparable accuracies to invasive point-of-care-devices. This is in spite of the fact that the described techniques make the prediction based only on fundus images of the patient's eye and demographic information for the patient.

FIG. 3B shows the accuracy of the described systems in predicting patient anemia. In particular, FIG. 3B shows receiver operating characteristic (ROC) curves for detecting anemia by a metadata-only model (black line), the fundus-only model (blue line), and the combined model (red line). The metadata-only model is a baseline model that makes predictions based only on additional patient data and not on fundus images. The fundus-only model is a model that uses only fundus images and no additional patient data. Area under the curve (AUC) for each model is shown with 95% confidence intervals. In particular, FIG. 3B includes three charts: a chart 350a that shows ROC curves and AUCs for detecting anemia, a chart 350b that shows ROC curves and AUCs for detecting moderate anemia, and a chart 350c that shows ROC curves and AUCs for detecting approximate anemia. As can be seen from FIG. 3B the combined and fundus-only models outperform the baseline metadata-only model on all three classification tasks, indicating that images of the fundus are used by the machine learning model to accurately classify anemia.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A system comprising one or more computers and one or more storage devices storing instructions that when executed by the one or more computers cause the one or more computers to perform operations comprising:
    obtaining a fundus image, the fundus image being an image of a fundus of an eye of a patient; and
    processing a model input comprising the fundus image using a fundus image processing neural network, wherein the fundus image processing neural network is configured to process the model input comprising the fundus image to generate a model output that predicts a property of the blood of the patient; and
    generating, from at least the model output, a final prediction of the property of the blood of the patient.

2. The system of claim 1, wherein the model input further comprises other patient data comprising patient demographic data.

3. The system of claim 2, wherein the fundus image processing neural network comprises a convolutional neural network and one or more fully-connected layers, and wherein the fundus image processing neural network is configured to:
    process the fundus image in the model input through the convolutional neural network to generate a convolutional output; and
    process the convolutional output and (i) the other patient data or (ii) data derived from the other patient data through the fully-connected layers to generate the model output.

4. The system of claim 1, wherein the fundus image processing neural network comprises a convolutional neural network and one or more fully-connected layers, and wherein the fundus image processing neural network is configured to:
    process the fundus image in the model input through the convolutional neural network to generate a convolutional output; and
    process the convolutional output through the fully-connected layers to generate the model output.

5. The system of claim 1, wherein the model output generated by the fundus image processing neural network by processing the model input comprising the fundus image comprises a predicted level of hemoglobin in the blood of the patient.

6. The system of claim 1, wherein the model output generated by the fundus image processing neural network by processing the model input comprising the fundus image comprises a predicted hematocrit of the blood of the patient.

7. The system of claim 1, wherein the model output generated by the fundus image processing neural network by processing the model input comprising the fundus image comprises a predicted red blood cell count of the blood of the patient.

8. The system of claim 1, wherein generating, from at least the model output, a final prediction of the property of the blood of the patient comprises:
    obtaining another fundus image, the other fundus image being an image of a fundus of the other eye of the patient; and
    processing another model input comprising the other fundus image using the fundus image processing neural network to generate another model output that predicts a property of the blood of the patient; and
    generating the final prediction from at least the model output and the other model output.

9. The system of claim 8, wherein the fundus image processing neural network is one of a plurality of neural networks in an ensemble of neural networks, and wherein generating, from at least the model output, a final prediction of the property of the blood of the patient comprises:
    processing the model input and the other model input using each other neural network in the ensemble to generate a respective model output and other model output for each of the other neural networks in the ensemble; and
    generating the final prediction by combining the model outputs and the other model outputs generated by all of the neural networks in the ensemble.

10. The system of claim 1, wherein the fundus image processing neural network is one of a plurality of neural networks in an ensemble of neural networks, and wherein generating, from at least the model output, a final prediction of the property of the blood of the patient comprises:
    processing the model input using each other neural network in the ensemble to generate a respective model output for each of the other neural networks in the ensemble; and
    generating the final prediction by combining the model outputs generated by all of the neural networks in the ensemble.

11. A system comprising one or more computers and one or more storage devices storing instructions that when executed by the one or more computers cause the one or more computers to perform operations comprising:
    obtaining a fundus image, the fundus image being an image of a fundus of an eye of a patient; and
    processing a model input comprising the fundus image using a fundus image processing neural network, wherein the fundus image processing neural network is configured to process the model input comprising the fundus image to generate a model output that predicts a current condition of the patient with respect to anemia; and
    generating, from at least the model output, a final prediction of the current condition with respect to anemia.

12. The system of claim 11, wherein the model input further comprises other patient data comprising patient demographic data.

13. The system of claim 12, wherein the fundus image processing neural network comprises a convolutional neural network and one or more fully-connected layers, and wherein the fundus image processing neural network is configured to:
  process the fundus image in the model input through the convolutional neural network to generate a convolutional output; and
  process the convolutional output and (i) the other patient data or (ii) data derived from the other patient data through the fully-connected layers to generate the model output.

14. The system of claim 11, wherein the fundus image processing neural network comprises a convolutional neural network and one or more fully-connected layers, and wherein the fundus image processing neural network is configured to:
  process the fundus image in the model input through the convolutional neural network to generate a convolutional output; and
  process the convolutional output through the fully-connected layers to generate the model output.

15. The system of claim 11, wherein the model output comprises a probability that the patient has anemia.

16. The system of claim 11, wherein the model output comprises a respective probability for each of multiple anemia classifications, and wherein the probability for a given disease state represents the predicted likelihood that the patient has the corresponding anemia classification.

17. The system of claim 16, wherein the anemia classifications comprise one or more of: anemia, moderate anemia, or approximate anemia.

18. The system of claim 11, wherein generating, from at least the model output, a final prediction comprises:
  obtaining another fundus image, the other fundus image being an image of a fundus of the other eye of the patient; and
  processing another model input comprising the other fundus image using the fundus image processing neural network to generate another model output; and
  generating the final prediction from at least the model output and the other model output.

19. The system of claim 18, wherein the fundus image processing neural network is one of a plurality of neural networks in an ensemble of neural networks, and wherein generating, from at least the model output, a final prediction comprises:
  processing the model input and the other model input using each other neural network in the ensemble to generate a respective model output and other model output for each of the other neural networks in the ensemble; and
  generating the final prediction by combining the model outputs and the other model outputs generated by all of the neural networks in the ensemble.

20. The system of claim 11, wherein the fundus image processing neural network is one of a plurality of neural networks in an ensemble of neural networks, and wherein generating, from at least the model output, a final prediction of the property of the blood of the patient comprises:
  processing the model input using each other neural network in the ensemble to generate a respective model output for each of the other neural networks in the ensemble; and
  generating the final prediction by combining the model outputs generated by all of the neural networks in the ensemble.

21. A method comprising:
  obtaining a fundus image, the fundus image being an image of a fundus of an eye of a patient; and
  processing a model input comprising the fundus image using a fundus image processing neural network, wherein the fundus image processing neural network is configured to process the model input comprising the fundus image to generate a model output that predicts a current condition of the patient with respect to anemia; and
  generating, from at least the model output, a final prediction of the current condition with respect to anemia.

* * * * *